United States Patent [19]

Sowerby

[11] Patent Number: 5,369,998
[45] Date of Patent: Dec. 6, 1994

[54] ULTRASONIC MASS FLOW METER FOR SOLIDS SUSPENDED IN A GAS STREAM

[75] Inventor: Brian Sowerby, Lucas Heights, Australia

[73] Assignee: Commonwealth Scientific and Industrial Research Organisation, Campbell, Australia

[21] Appl. No.: 207,109

[22] Filed: Mar. 8, 1994

Related U.S. Application Data

[63] Continuation of Ser. No. 867,217, filed as PCT/AU90/00587, Dec. 11, 1990, published as WO87/05696, Sep. 24, 1987, abandoned.

[30] Foreign Application Priority Data

Dec. 12, 1989 [AU] Australia ......................... PJ7806

[51] Int. Cl.$^5$ ........................... G01F 1/74; G01F 1/66
[52] U.S. Cl. ................... 73/861.04; 73/861.28
[58] Field of Search ............ 73/861.04, 861.27, 861.28

[56] References Cited

U.S. PATENT DOCUMENTS

| | | | |
|---|---|---|---|
| 4,545,244 | 10/1985 | Yasuda et al. | 73/861.28 |
| 4,581,942 | 4/1986 | Ogura et al. | 73/861.04 |
| 4,726,235 | 2/1988 | Leffert et al. | 73/861.04 |
| 4,882,934 | 11/1989 | Leffert et al. | 73/861.04 |

FOREIGN PATENT DOCUMENTS

| | | | |
|---|---|---|---|
| 0094148 | 11/1983 | European Pat. Off. | 73/861.29 |
| 8705696 | 9/1987 | WIPO | |

OTHER PUBLICATIONS

Patent Abstracts of Japan, E-77, p. 4782, JP A 52-50784; Hokushin Denki Seisakusho K.K., 23 Apr. 1977.

Lynnworth, "Ultrasonic Flowmeters", Trans. Inst. M C, vol. 3, No. 4, 1981, pp. 217–223.

Primary Examiner—Richard E. Chilcot, Jr.
Assistant Examiner—William L. Oen
Attorney, Agent, or Firm—Leydig, Voit & Mayer

[57] ABSTRACT

Method and apparatus (1) for measuring the mass flow rate of solids suspended in a gas stream (2) flowing along a pipe (3). Two ultrasonic transducers (4, 5) are mounted in short side arms (6, 7) extending from the pipe. The transducers are arranged such that signals are transmitted from one to the other through the gas stream at an angle $\Theta$, usually about 45°. The received signals in both transducers are received by apparatus (8) and amplified. The invention allows determination of: the mean times for the ultrasonic pulses to travel from one transducer (4) to another (5) and vice-versa; the mean peak amplitude of received pulses; and, the standard deviation or spread of these parameters. The mean times taken for the ultrasonic signals to travel between the transducers are used to determine the gas flow velocity, and the mean peak amplitudes for calculating the solids loading. From these the mass flow rate is derived. The invention is applicable to determining mass flow rates of pulverised coal contained in an air flow in a large power station.

17 Claims, 7 Drawing Sheets

ULTRASONIC MASS FLOW METER FOR SOLIDS SUSPENDED IN A GAS STREAM

This disclosure is a continuation of application Ser. No. 07/ 867,217, filed as PCT/AU90/00587, Dec. 11, 1990, published as WO87/05696, Sep. 24, 1987, now abandoned.

TECHNICAL FIELD

This invention relates to a method and apparatus to measure the mass flow rates of solids suspended in a gas stream. The invention is particularly applicable to the measurement of the mass flow rate of pulverized coal in air in large power stations. Although the invention is described with reference to this application it will be appreciated that the invention is equally applicable to measurement of the mass flow rate of other solids suspended in a gas stream.

BACKGROUND ART

In coal-fired boilers of the type typically used to generate electricity, coal is pulverized in mills and then transported pneumatically via heated primary air through burner feed pipes to burners within the boiler. A typical large coal-fired boiler will operate with about seven pulverizer mills and 40 burners. The mills pulverize the feed coal to a particle size of about 75% through a 75 $\mu$m screen, degrading to about 40% through a 75 $\mu$m screen when the mill becomes worn. The coal-air mixture is blown out of the mill into about six burner feed pipes of diameter 300 to 600 mm at velocities of about 25 m/sec. The coal/air mass ratio in these feed pipes is about 0.8.

A significant problem for large coal-fired boiler operation arises from non-uniform splitting of the pulverized coal between the burner feed pipes. This can lead to localized areas of incomplete combustion, slagging and fouling, increased $NO_x$ emissions and a reduction in boiler efficiency.

In present practice, the coal flow rate into the pulverizer mills can be monitored with gravimetric feeders. The primary air flow rates from each mill are balanced before coal is added using standard pitot tube flow meters. However this method does not measure coal loading and continuous readings during boiler operation are not feasible.

There is a clear need for a reliable and accurate on-line instrument to measure to within about 5% the relative mass flow rates of pulverized coal in feed pipes into large coal-fired boilers. The measurement technique should preferably be non-invasive, accurate and relatively inexpensive.

A Patent Co-operation Treaty application published under no. WO 87/05696 and U.S. Pat. No. 4,882,934 describe meters in which a narrow ultrasonic beam (angular spread 4°) of frequency 460kHz is transmitted at 90° to the flow direction and flow velocity is determined from the downstream drift of the beam which is measured by physically moving the ultrasonic receivers. Solids loading is measured from the mean attenuation of the transmitted ultrasonic beam. The main disadvantage of this technique is the need to constantly move the ultrasonic receivers to determine the peak signal amplitude of the highly fluctuating partly attenuated signal. The signal is highly fluctuating partly because of the narrow ultrasonic beam which must be used in this system. Typically about 50 pulse amplitude measurements are required at each of 30 receiver locations, making a total of 1500 measurements for each determination of coal mass flow. The technique is therefore relatively complex and it has difficulty in measuring rapid changes in velocity and mass loading. As well, the downstream drift distance used to measure velocity is affected by changes in gas temperature and a correction is required.

The British Coal Utilisation Research Association (BCURA) has developed and field tested a pulverized coal mass flow meter comprising an ultrasonic gas velocity meter combined with a beta-particle absorption meter for coal density. The ultrasonic meter comprises two pairs of ultrasonic transducers with 40kHz continuous ultrasonic waves transmitted upstream and downstream at about 45° to the flow direction. The gas velocity was derived from the phase difference between the two received signals. The BCURA pulverized fuel mass flow meter has been evaluated and, although it has some problems, it has been shown to be capable of measuring the mass flow to individual burners to within about ±10%. The BCURA mass flow meters have also been field tested at a British power station. However there was sufficient erosion and build-up on the sensor faces in these field tests that the mass flow meter was not recommended for industrial use. In practice, the major disadvantage of the BCURA meter is the hazard of using radioactive beta-ray sources separated from an abrasive and hostile atmosphere by only thin windows.

DISCLOSURE OF THE INVENTION

It is an object of this invention to provide a method and apparatus to measure the mass flow rate of solids suspended in a gas stream which will overcome or at least ameliorate the disadvantages of the prior art and address the above need for a reliable and accurate on-line instrument.

Accordingly, one aspect of this invention is a method of measuring the mass flow rate of solids suspended in a gas stream comprising the steps of transmitting ultrasonic signals through the gas stream in opposing directions oblique to the flow direction, receiving the transmitted signals, determining the respective transit times of the signals and deriving from the transit times a measure of gas flow velocity; determining a measure of solids loading in the stream from the attenuation of an ultrasonic signal transmitted through the gas stream; and thereby determining the mass flow rate of solids from the measure of gas flow velocity and measure of solids loading.

A second aspect of this invention is an apparatus to measure the mass flow rate of solids suspended in a gas stream comprising ultrasonic transmitting and receiving means respectively to direct ultrasonic signals through the gas stream in opposing directions oblique to the flow direction and receive the transmitted signals; means to determine the respective transit times of the signals and derive from the transit times a measure of gas flow velocity; means to determine a measure of solids loading in the stream from the attenuation of an ultrasonic signal transmitted through the gas stream; and processing means to determine the mass flow rate of solids from the measure of gas flow velocity and measure of solids loading.

Preferably, the ultrasonic signals travel in opposing directions along substantially the same path. This can, for example, be achieved by using two ultrasonic transducers positioned on opposite sides of the pipe or duct containing the gas stream and disposed such that the ultrasonic signal is transmitted obliquely to the flow direction. In this configuration both transducers act as transmitters and receivers of ultrasonic radiation.

Preferably, the signal whose attenuation is to be determined is transmitted and received perpendicular to the flow direction. Preferably also, the ultrasonic transducers are flush mounted with the pipe or duct containing the gas stream.

In another embodiment of the invention, two pairs of transducers can be used to measure upstream transmission, respectively and downstream transmission, respectively.

In a further form of the invention, the ultrasonic signals can travel in opposing directions along different paths. This can, for example, be achieved by using a very broad beam transmitter (say 90°) and separate receivers, one located downstream and the other upstream.

Multiple pairs of transducers can be used in any of the above configurations to obtain average flow data over a larger fraction of the cross section of the pipe or duct conveying the gas stream.

It is preferred that the ultrasonic signals are transmitted at about 45° to the flow direction of the gas stream.

Preferably, the ultrasonic transducers are broad-beam transducers. That is, the transducers have greater than a 10° spread in the output radiation. Broad beam transducers have the advantage of being less affected than narrow beam transducers by refraction and scattering in turbulent eddies.

The transducers preferably produce ultrasonic radiation having a frequency in the range of 100 to 500 kHz. The transducers are preferably piezoelectric material although some other types of ultrasonic transmitters and receivers are suitable. The transducers are pulsed either simultaneously or sequentially at a pulse rate appreciably lower than the ultrasonic frequency of 100 to 500 kHz, preferably at about 100 Hz.

Preferably, the measures of gas flow velocity and solids loading are derived from measurements of the mean and standard deviations, or other measures of spread, of ultrasonic pulse transit times and amplitude attenuation, respectively.

In the preferred embodiment, the ultrasonic waveforms received by the two transducers are amplified and analyzed to accurately determine arrival time and pulse height. Preferably, ultrasonic waveforms for time determination are accepted only if certain criteria are met such as: a certain number of peaks before maximum voltage reached; a spacing of peaks consistent with the ultrasonic frequency; and that peak heights ascend up to the maximum voltage.

In a preferred form, the invention further comprises means for determining the temperature of the gas stream from the transit times and correcting the measure of solids loading for temperature dependent variations in attenuation of the transmitted ultrasonic signal.

It is further preferred that the invention comprises compensating the measure of solids loading for turbulence induced variation in attenuation of the transmitted ultrasonic signal.

Preferably, the transducers are located in special recesses for preventing the build up of particles around the transducers. Such recesses would allow flush mounting the transducers which relay the attenuation signal at 90° to the direction of flow of the gas stream.

Another alternative would include wedge shaped interface material mounted flush with the pipe or duct carrying the gas stream. After refraction, the ultrasonic wave is received by a corresponding wedge/receiver combination.

It will be apparent that this invention provides a method and apparatus for on-line measurement of mass flow rate which is non-invasive and relatively inexpensive. The invention overcomes major disadvantages of prior art techniques in that neither movable transducers nor radioactive sources are required.

BRIEF DESCRIPTION OF THE DRAWINGS

One embodiment of this invention will now be described, by way of example only, with reference to the accompanying drawings in which.

MODES FOR CARRYING OUT THE INVENTION

Figure 1:
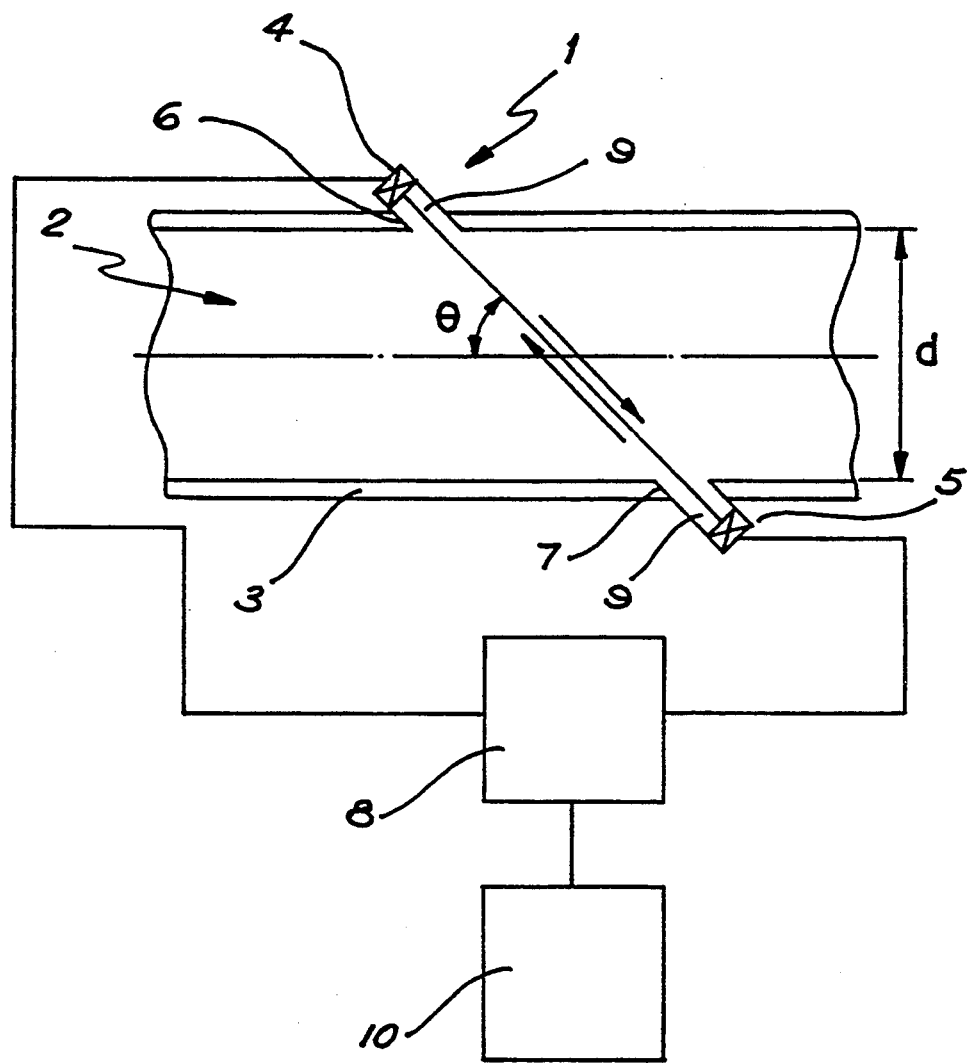
FIG. 1 is a schematic diagram of an apparatus to measure mass flow rate fitted to a pipe of diameter d carrying solids suspended in a gas stream.

As shown in FIG. 1, the apparatus 1 to measure mass flow rate of solids suspended in a gas stream 2 flowing along a pipe 3 of diameter d comprises two ultrasonic transducers 4 and 5 mounted in short side arms 6 and 7 extending from the pipe. The transducers are arranged such that ultrasonic signals are transmitted from one to the other through the gas stream at an angle $\theta$, usually about 45°.

The transducers 4 and 5 are 215 kHz lead zirconate titanate (PZT) broad beam transducers having a greater than 10° spread to minimize refraction and scattering in turbulent eddies. The transducers are driven either sequentially or simultaneously to produce ultrasonic wave packets having a duration of about 20 microseconds. The received signals in both transducers are received by apparatus 8 where they are amplified and the following parameters are measured: the mean times for the ultrasonic pulses to travel from transducer 4 to transducer 5($t_{45}$) and vice-versa ($t_{54}$); the mean peak amplitude of received pulses (A); and the standard deviations or spread of these parameters ($\Delta t_{45}$, $\Delta t_{54}$ and $\Delta A$, respectively).

The velocity of gas flow (V) is determined from the equation:

$$V = \frac{d}{2\sin\theta \cos\theta} \left[ \frac{1}{t_{54}} - \frac{1}{t_{45}} \right] \tag{1}$$

where d is the pipe diameter and $\theta$ the angle between the mean flow direction and ultrasonic beam direction. Minor corrections are made to the transit times $t_{45}$ and $t_{54}$ and diameter d to account for the dead space 9 in front of the transducers. The flow velocity V determined using equation (1) is independent of the velocity of sound (c) in the medium and therefore independent of gas temperature. The determination of single phase flow velocity using equation (1) is well known to those skilled in the art.

The mean velocity of solids in the gas stream will normally be a fixed fraction of the velocity of the gas stream. In all practical situations in power stations, the mean velocity of pulverized coal is 98 to 99% of the air velocity.

The solids loading in the gas ($\rho$) is derived from measurements of the mean ultrasonic amplitude ratio $A/A_o$ with corrections applied for ultrasound attenuation due to turbulence. The amplitude A is that measured with solids suspended in the gas stream and $A_o$ is the amplitude measured with still gas in the pipe 3. Once V and $\rho$ are determined, the mass flow rate of solids (M) can be determined from the equation:

$$M = \rho V \cdot \pi \cdot (d/2)^2 \tag{2}$$

The amplitude ratio is given by the equation:

$$\frac{A}{A_o} = \exp\left[ -2 \cdot \alpha \cdot \frac{d}{\sin\theta} \right] \tag{3}$$

where $\alpha$ = total attenuation coefficient and $d/\sin\theta$ = distance travelled by the sound in the medium.

It is customary to express sound attenuation in logarithmic intensity levels (L) in units of decibels (db)

$$L = -10 \log_{10}(A/A_s) \tag{4}$$

where $A_s$ is the amplitude of a standard reference signal, which in the present application can be taken as being equal to $A_o$.

The total attenuation coefficient is the sum of individual attenuation coefficients due to the various physical phenomena that attenuate the sound, namely, $$\alpha = \alpha_g + \alpha_t + \alpha_s \tag{5}$$

where $\alpha_g$, the attenuation coefficient due to still gas, is a function of humidity and temperature;

$\alpha_t$, the attenuation coefficient due to turbulence, is a function of gas velocity and temperature in a particular physical pipe configuration;

$\alpha_s$, the attenuation coefficient due to suspended solids, is a function of solids loading ($\rho$) and particle size distribution.

In the present method, gas temperature in degrees centigrade can be accurately measured from the velocity of sound in the medium (c in m/sec) using the equation:

$$T = \left[ \frac{c^2}{109296} - 1 \right] / 0.0037 \tag{6}$$

where $c = d/(t_{45}\sin\theta) - V \cos\theta$.

In practice in a power station application, $\alpha_g$ is measured from the attenuation of ultrasound in still air of temperature and humidity similar to that found in pulverized coal feed lines. Variations in $\alpha_g$ due to temperature can be calculated from the measured temperature (equation (6)). Variations in $\alpha_g$ due to humidity variations in power station primary air are not significant.

Turbulence in the pipe causes refraction and scattering of the ultrasound beams traversing the pipe 3. This turbulence can be characterized by the measured values of flow velocity (equation (1)), temperature (equation (6)), and the standard deviations in measured transit time and amplitude ($\Delta t_{45}$ and $\Delta A$). The coefficients in the equation relating $\alpha_t$ to the parameters V, T, $\Delta t_{45}$ and $\Delta t_{45}$ and $\Delta A$ are determined experimentally during the calibration of the ultrasonic mass flow meter. This calibration can be carried out by comparing total ultrasound attenuation with separate measurements of solids loading over a range of conditions (e.g. temperature, velocity, and solids, loading). The separate measurement of solids loading can be beta-particle transmission, physical sampling or another suitable method. Beta-particle transmission along a path similar to the ultrasound path is preferred. These separate calibration measurements of $\alpha_s$ and the previous measurement of $\alpha_g$ on still air permit $\alpha_t$ to be predicted as a function of V, T, $\Delta t_{45}$ and $\Delta A$.

The attenuation coefficient $\alpha_s$ is dependent on solids loading and particle size. However results obtained show that particle size variations normally encountered in a pulverized coal feed to a power station will cause only small errors in the determination of $\alpha_s$ and coal loading. In practice, these small errors can be overcome by infrequent recalibration.

The operation of the apparatus of FIG. 1 used to determine mass flow rate can thus be summarized as follows:

(a) The transducers 4 and 5 are driven either sequentially or simultaneously to produce ultrasonic wave packets with a duration of about 20 microseconds.

(b) The received signals in both transducers are amplified by apparatus 8 and each wave packet subjected to selection criteria before determining crossover time.

(c) Steps (a) and (b) are repeated about 100 times at a repetition frequency of about 100 Hz. The mean times and amplitudes and their standard deviations are calculated by apparatus 10.

(d) Flow velocity (equation (1)) and temperature (equation (6)) are determined from measured transit times by apparatus 10.

(e) Solids loading is determined by apparatus 10 from the attenuation of ultrasound in the medium and the total attenuation coefficient $\alpha$(equation 3), knowing $\alpha_g$ from calibration and $\alpha_t$ from V, T, $\Delta t_{45}$ and $\Delta A$.

(f) Steps (a) to (e) are repeated to update readings as required.

It will be apparent that calibration of the ultrasonic gauge will involve measurements in still air to determine $\alpha_g$ and independent measurements of solids loading, preferably using beta-particle transmission.

Figure 2:
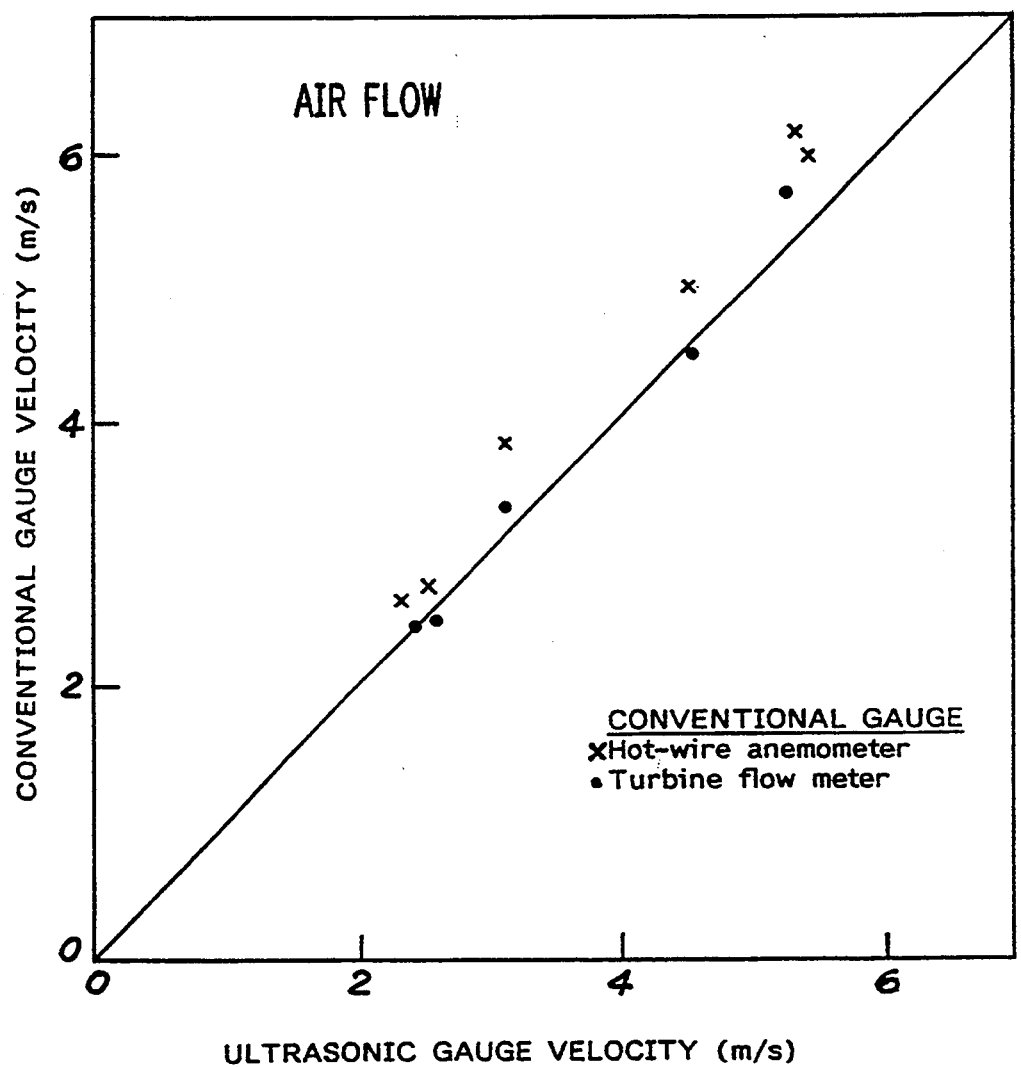
FIG. 2 is a graphic comparison of air velocity measured by the apparatus of FIG. 1 with that measured by a conventional hot wire anemometer and a turbine flow meter.

Measurements have been carried out using an apparatus as shown in FIG. 1 in which the pipe diameter was 300 mm, and the length was 1.5 m. A variable speed fan was mounted at one end of the pipe to create an air flow. The two 215 kHz PZT transducers 4 and 5 were mounted at 45° to the flow direction as shown in FIG. 1. Air velocity in the pipe was varied in the range 0 to 6 m/s under conditions of varying turbulence and temperature. Turbulence was varied by changing the air inlet aperture to the pipe and temperature was varied by passing all or part of the inlet air through fan heaters. At a flow velocity of 5.4 m/s, typical values of $t_{45}$ and $t_{54}$ are 1.446 and 1.414 milliseconds, respectively. Air velocity was also measured using a conventional hot-wire anemometer and a hand-held turbine flow meter. The velocity measured using the ultrasonic technique (equation(1)) agreed with that measured with the other meters, as shown graphically in FIG. 2. This agreement was satisfactory considering that the hot-wire anemometer measures the flow in one location whereas the ultrasonic technique gives an average velocity across the pipe. The turbine flow meter was only able to be used on measurements with an open 300 mm diameter pipe. The measurements in FIG. 2 were carried out with air temperatures in the range 11° C. to 48° C. These measurements confirmed that the ultrasonic technique measures flow independent of air temperature.

Figure 3:
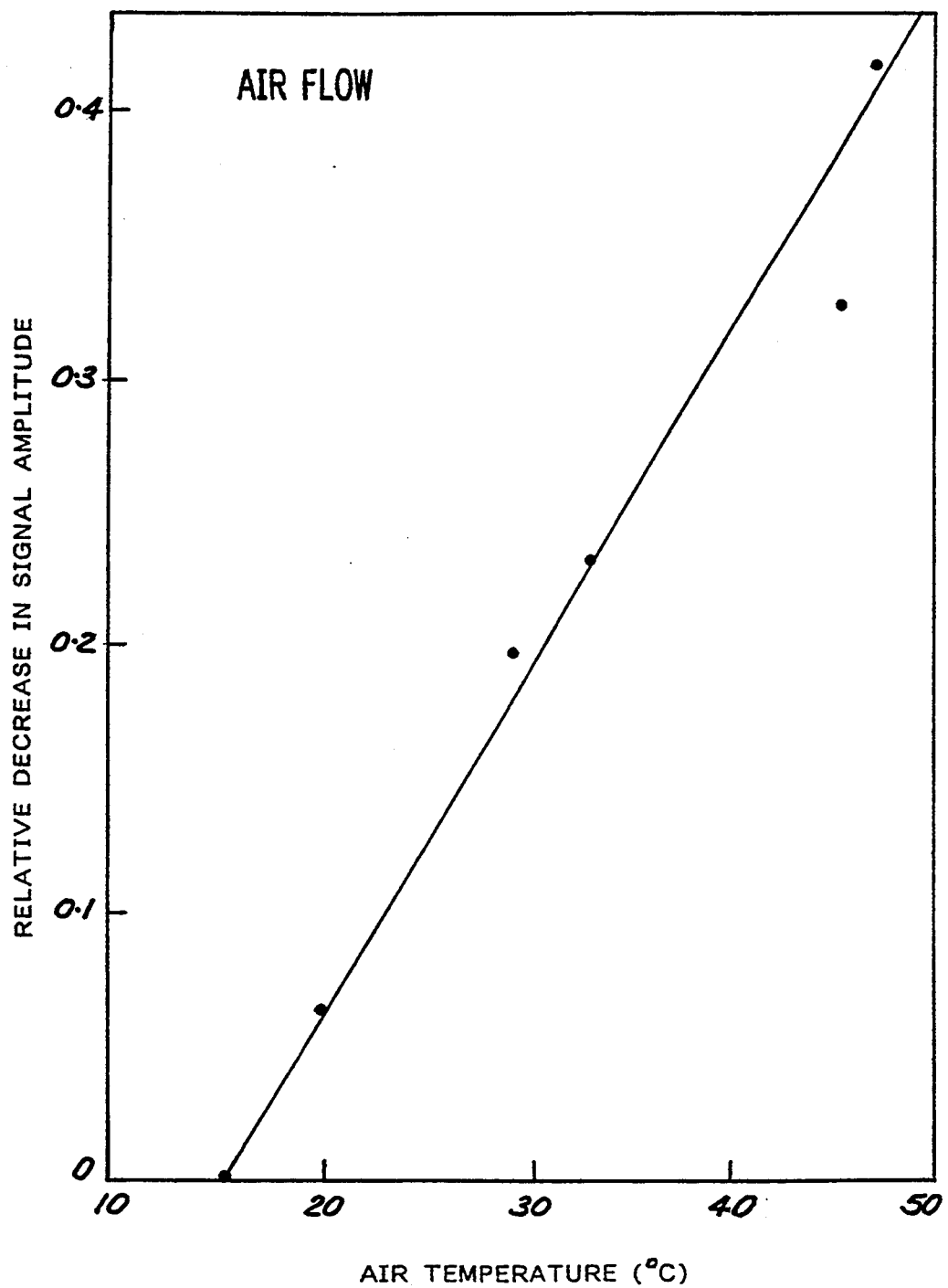
FIG. 3 is a graphic representation of relative decrease in mean ultrasonic signal amplitude as a function of air temperature for various flow conditions and velocities of air in a 300 mm diameter pipe.

The amplitude of ultrasonic signals measured with air flowing in the pipe is lower than that measured with still air. This decreased amplitude is due to flow turbulence and temperature turbulence. Of these, the component due to temperature turbulence, as shown graphically in FIG. 3, is the largest. The flow and temperature turbulence can be corrected using the measured values of flow and temperature from equations (1) and (6), respectively.

Figure 4:
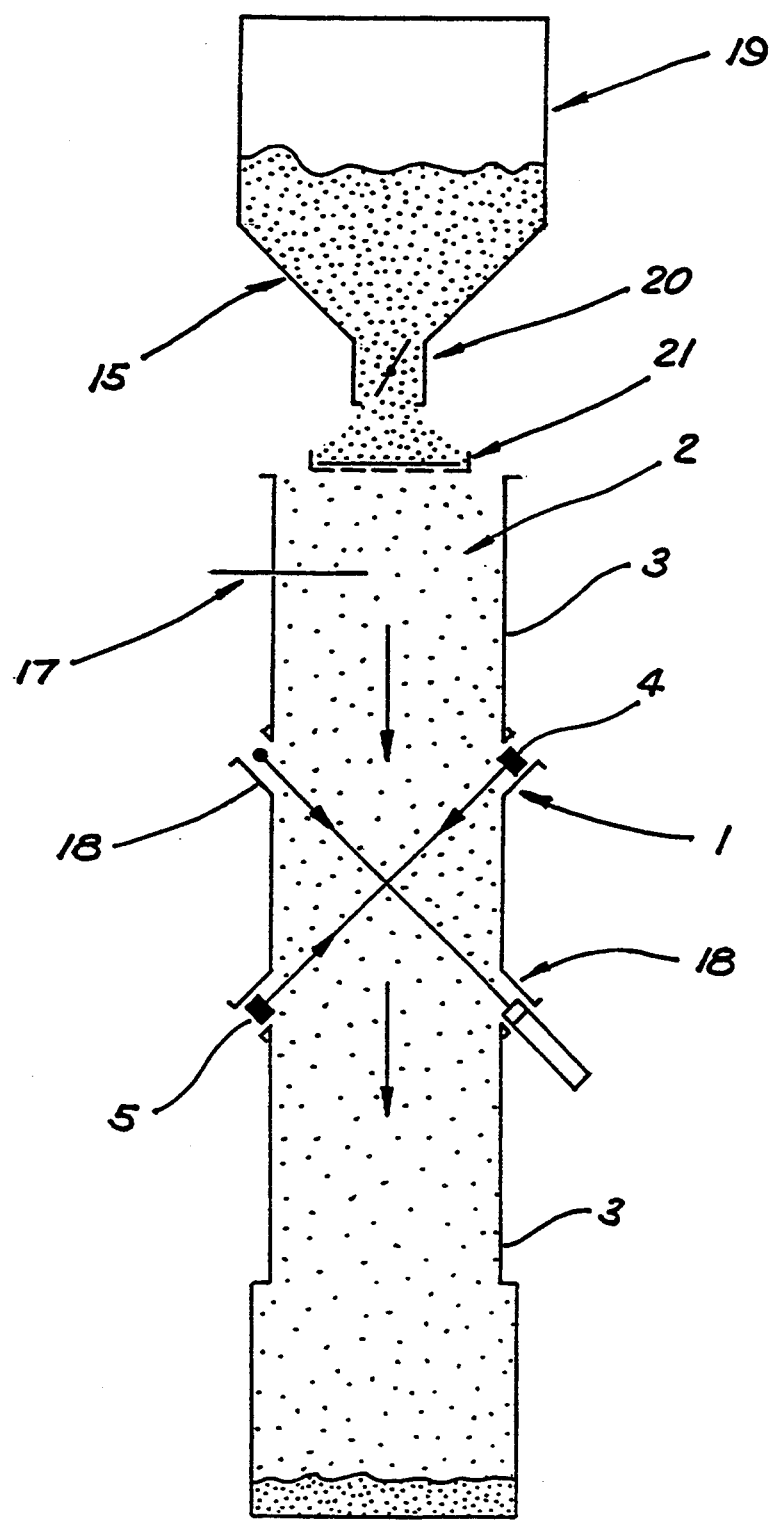
FIG. 4 is a schematic diagram of an apparatus used in laboratory experiments to determine the effect of solids loading on ultrasound transmission.

FIG. 4 shows an experimental arrangement used to measure the effect of suspended solids on the transmission of ultrasound. The arrangement is the same as described above and corresponding features are denoted with corresponding reference numerals. The 300 mm diameter pipe 3 is mounted vertically and feed equipment 15 uniformly feeds dust into the pipe. This dust falls under gravity past a temperature probe 17, the ultrasonic transducers 4 and 5 and a beta-particle transmission gauge 18 mounted at 45° across the tube in the same vertical plane as the ultrasonic transducers. The feed equipment includes a reservoir 19 for containing dust, a valve 20 to regulate the dust flow from the reservoir and a sieve and spreader combination 21 for spreading the dust across the pipe.

Figure 5A:
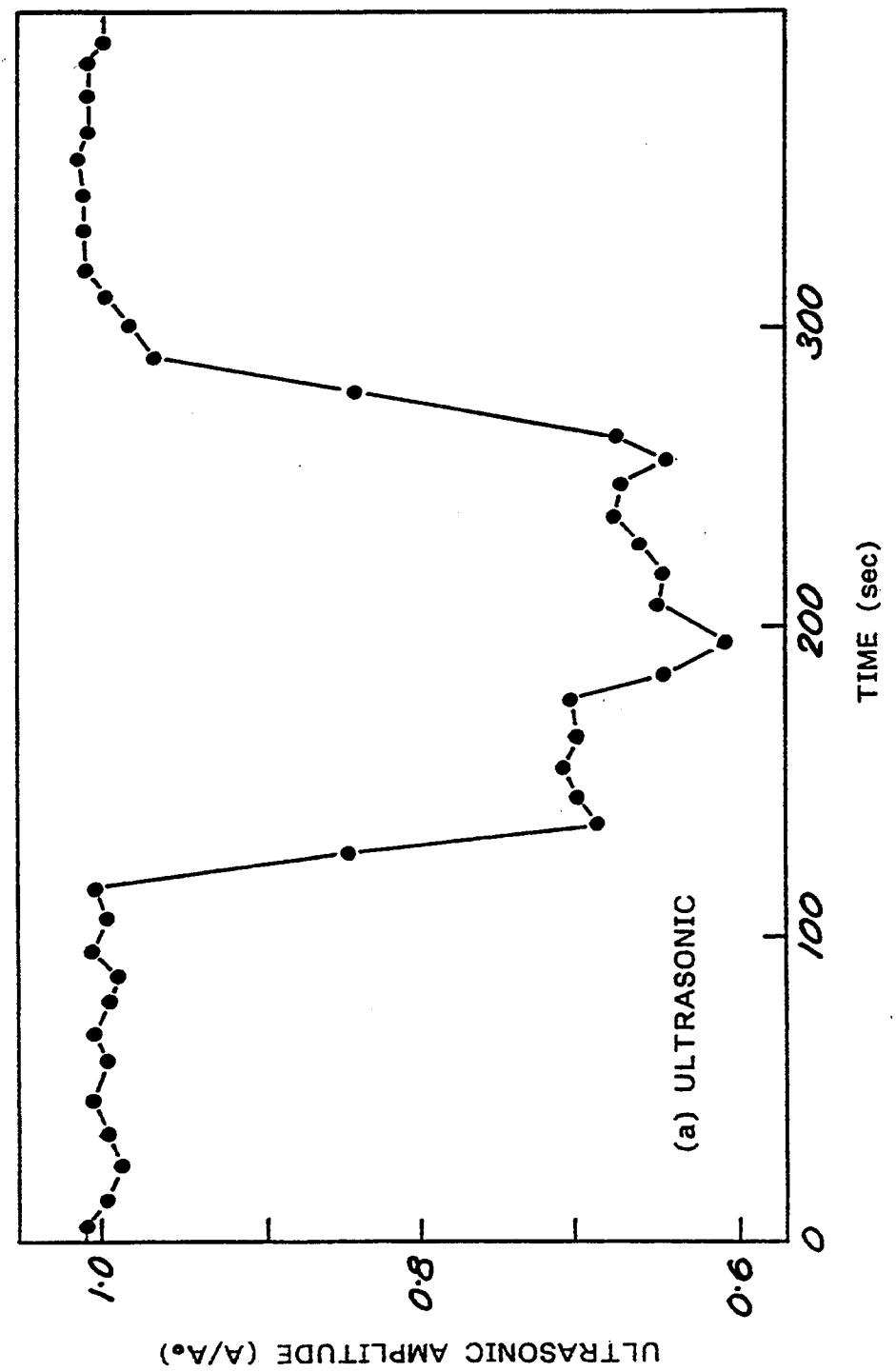
FIG. 5($a$) is a graph showing the effect of suspended solids on ultrasonic signal amplitude and FIG. 5($b$) is a graph showing the effect of suspended solids on beta-particle transmission count rate.
Figure 5B:
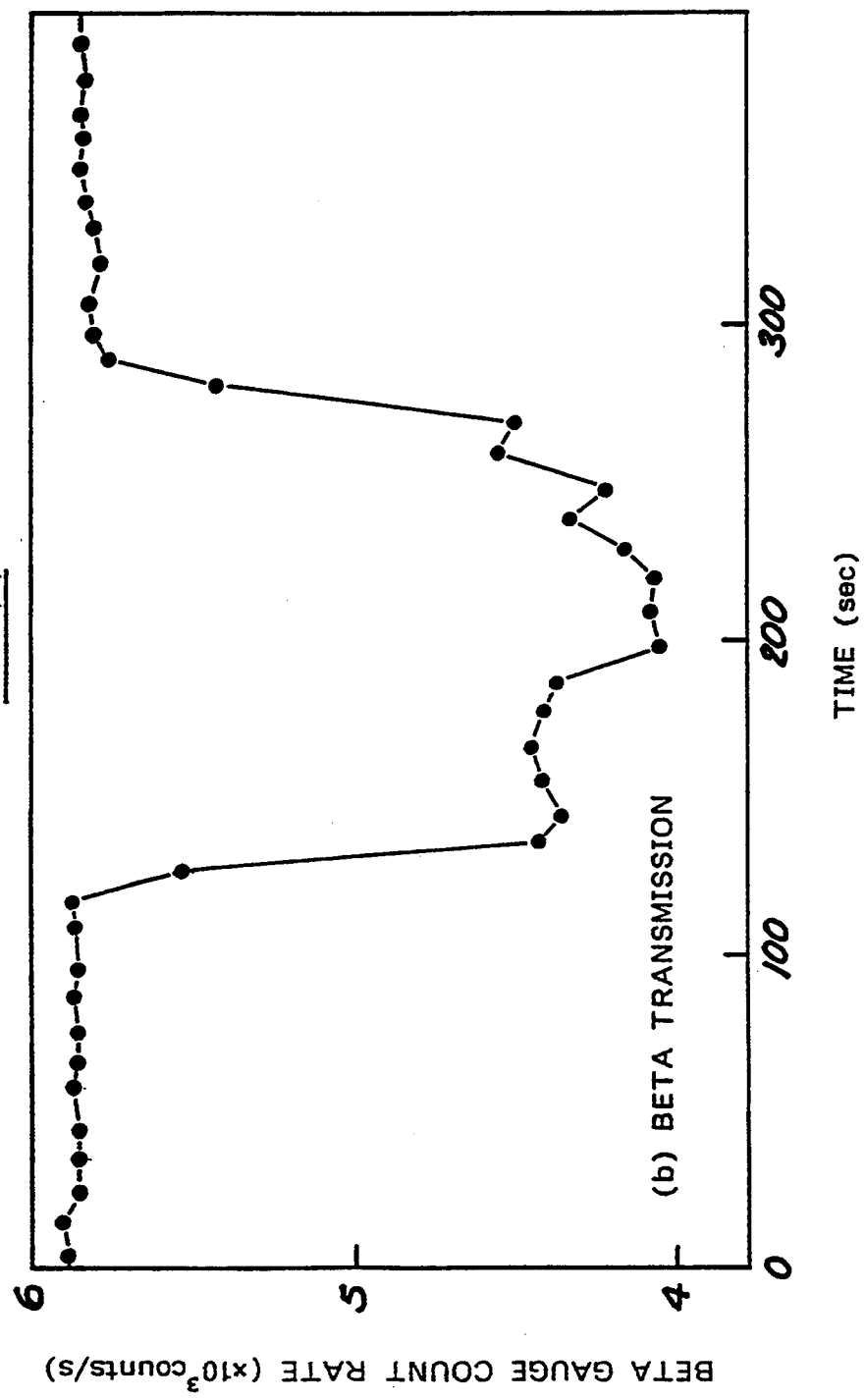

The beta-particle gauge was calibrated in-situ in a dust free environment using plastic sheets of known thickness. Typical outputs of beta gauge count rate and ultrasonic amplitude versus time are shown in FIGS. 5(a) and (b). Between 120 and 280 seconds, about 5 kg of fine alumina passed through the 300 mm pipe. Before 120 seconds and after 280 seconds there was no suspended dust in the tube.

The outputs of both gauges 1 and 18 were measured for various loadings of alumina dust of various known particle size distributions. The dust particle size distributions were:

Dust A: 95% of mass less than 150 $\mu$m, 30% less than 75$\mu$m, 5% less than 45 $\mu$m Dust B: 99% less than 45 $\mu$m Dust C: 90% less than 10 $\mu$m, 16% less than 1 $\mu$m.

Figure 6:
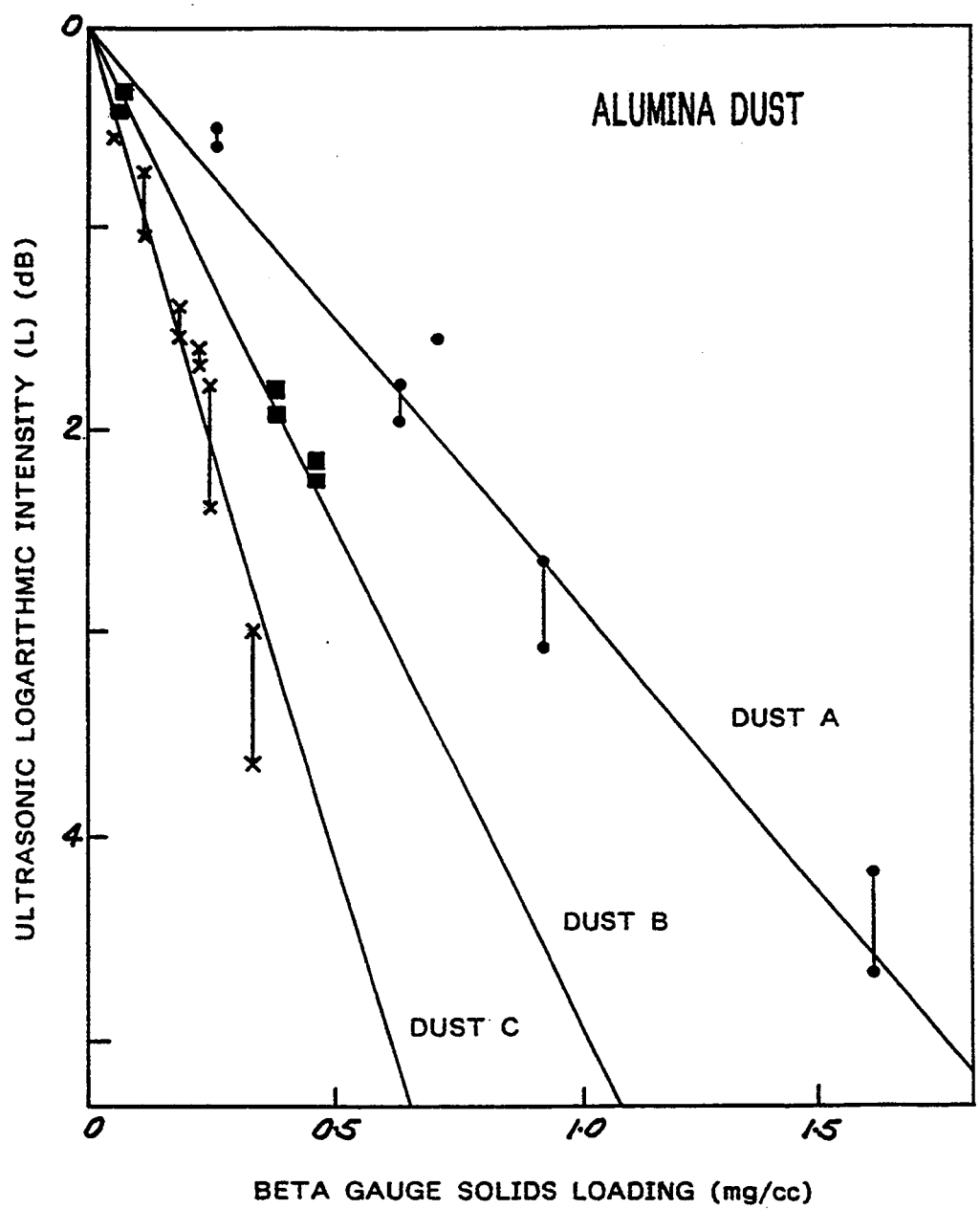
FIG. 6 is a plot of ultrasonic logarithmic intensity (L) versus solids loading (measured using a beta-particle transmission gauge) for three alumina dust samples of different particle size ranges.

The results of ultrasonic attenuation measurements versus dust density measured with the beta transmission gauge are shown in FIG. 6. The net flow rate of air in the tube is close to zero although the dust itself will drop at velocities up to its terminal velocity under gravity in still air (maximum of about 0.5 m/sec).

The particle size variation in the alumina dust used in the above experiment is much greater than would be encountered in a coal-fired power station. An unworn pulverizer mill in a power station will typically produce pulverized coal with 75% of the mass of coal being of particle size less than 75 $\mu$m. This fraction of minus 75 $\mu$m coal will typically decrease to about 40% over the life of the mill. The effect of this increase in particle is calculated to be a 7% increase in ultrasonic signal over the life of the mill at a constant solids loading of 1 mg $cm^{-3}$. This small error can be corrected by infrequent recalibration of the ultrasonic gauge over the life of the mill.

The foregoing describes only one embodiment of this invention and modifications can be made without departing from the scope of the invention. For example, using wedge shaped portions of materials such as polyurethane, polyethylene, liquids, metals and other suitable materials for flush mounting any of the ultrasonic transducers with the pipe containing the gas stream prevents the build up of particles around the transducer. The ultrasonic signal, after being refracted by the wedge, can be detected by a corresponding wedge/receiver unit suitably placed along the pipe or duct containing the gas stream. Furthermore, separate amplitude measurement transducers being perpendicularly mounted to the direction of the gas flow are within the scope of the invention.

Furthermore, a second transducer pair respectively transmitting an ultrasonic signal perpendicularly to the flow direction and subsequently receiving the signal and obtaining the amplitude would be within the scope of the invention. Such transducers are flush mounted with the pipe containing the gas stream for preventing particle build up around the transducer.

I claim:

1. An apparatus to measure the mass flow rate of solids suspended in a gas stream flowing through a pipe, the apparatus comprising:

ultrasonic transmitting and receiving means, each fixedly disposed on said pipe to respectively direct and receive ultrasonic signals through said gas stream in opposing directions oblique to the flow direction;

means to determine the respective transit times of said signals and derive from said transit times a measure of gas flow velocity using the following equation:

$$V = \frac{d}{2\text{SIN}\theta \, \text{COS}\theta} \left[ \frac{1}{t_{54}} - \frac{1}{t_{45}} \right],$$

where d is the diameter of the pipe, $\Theta$ is the angle between the flow direction and the direction of the ultrasonic signals, $t_{54}$ is the transmit time from the first transducer to the second transducer, and $t_{45}$ is the transit time from the second transducer to the first transducer;

means to determine a measure of solids loading in said stream from the attenuation of an ultrasonic signal transmitted through said gas stream; and processing means to determine the mass flow rate of solids from said measure of gas flow velocity and measure of solids loading.

2. Apparatus according to claim 1 wherein said ultrasonic signals travel in opposing directions along substantially the same respective paths.

3. Apparatus according to claim 1 wherein said means to determine the attenuation of an ultrasonic signal is responsive to said ultrasonic signal transmitted obliquely through said gas stream.

4. Apparatus according to claim 1 wherein said means to determine a measure of solids loading is responsive to the attenuation of an ultrasonic signal transmitted perpendicularly to said flow direction.

5. Apparatus according to claim 1 wherein a plurality of pairs of transducers are used to obtain average flow data.

6. Apparatus according claim 1 wherein said ultrasonic signals travelling in oblique directions are transmitted at substantially 45 degrees to the flow direction of the gas stream.

7. Apparatus according to claim 1 wherein said ultrasonic transducers are broad beam transducers having an output radiation spread greater than 10 degrees.

8. Apparatus according to claim 1 wherein said ultrasonic radiation has a frequency in the range of 100 to 500 kHz.

9. Apparatus according to claim 1 wherein at least one of said ultrasonic transmitting and receiving means are flush mounted to the pipe or duct containing said gas flow.

10. Apparatus according to claim 9 wherein said mounting includes a wedged shaped interface material.

11. Apparatus according to claim 10 wherein said interface material includes polyurethane.

12. Apparatus according to claim 1 including means for determining the temperature of the gas stream from the transit times and correcting the measure of solids loading for temperature dependent variations in attenuation of the transmitted ultrasonic signal.

13. Apparatus according to claim 12 including means for compensating the measure of solids loading for turbulence induced variation in attenuation of the transmitted ultrasonic signal.

14. A method of measuring the mass flow rate of solids suspended in a gas stream, the method comprising:

transmitting ultrasonic signals through said gas stream in opposing directions oblique to the flow direction;

receiving the transmitted signals using first and second fixed position transducers;

determining the respective transit times of said signals;

deriving from said transit times a measure of gas flow velocity using the following equation:

$$V = \frac{d}{2\mathrm{SIN}\theta\,\mathrm{COS}\theta}\left[\frac{1}{t_{54}} - \frac{1}{t_{45}}\right],$$

where d is the diameter of the pipe, $\theta$ is the angle between the flow direction and the direction of the ultrasonic signals, $t_{54}$ is the transmit time from the first transducer to the second transducer, and $t_{45}$ is the transmit time from the second transducer to the first transducer;

determining a measure of solids loading in said stream from the attenuation of an ultrasonic signal transmitted through said gas stream; and determining the mass flow rate of solids from said measure of gas flow velocity and measure of solids loading.

15. A method according to claim 14 wherein said ultrasonic signals travel in opposing directions along substantially the same respective paths.

16. A method according to claim 14 wherein the attenuation is obtained from an ultrasonic signal transmitted obliquely through said gas stream.

17. An apparatus for measuring the mass flow rate of solids suspended in a gas stream flowing through a pipe having a diameter d, the apparatus comprising:

first and second ultrasonic transducers, disposed on the pipe, transmitting ultrasonic signals through the gas stream in opposing directions oblique to the flow direction, where $\theta$ is the angle between flow directions and the direction of the ultrasonic signals, the first and second ultrasonic transducers being oppositely disposed in fixed relation to each other and to the pipe, the transmit time from the first transducer to the second transducer being $t_{54}$ and the transmit time from the second transducer to the first transducer being $t_{45}$;

a computer, coupled to the ultrasonic transmitter and to the ultrasonic receiver, determining the transmit times of the ultrasonic signals, deriving from the transmit times a measure of gas flow velocity using the following equation:

$$V = \frac{d}{2\mathrm{SIN}\theta\,\mathrm{COS}\theta}\left[\frac{1}{t_{54}} - \frac{1}{t_{45}}\right]$$

determining a measure of solids loading in the gas stream from attenuation of an ultrasonic signal transmitted through the gas stream, and determining the mass flow rate of solids from the measure of gas flow velocity and the measure of solids loading.

* * * * *

UNITED STATES PATENT AND TRADEMARK OFFICE
CERTIFICATE OF CORRECTION

PATENT NO. : 5,369,998
DATED : December 6, 1994
INVENTOR(S) : Brian Sowerby

It is certified that error appears in the above-indentified patent and that said Letters Patent is hereby corrected as shown below:

Title Page:
In item [63], Related U.S. Application Data, line 3, delete "published as WO87/05696, Sep. 24, 1987".

Column 9, line 21, after "according" insert --to--.

Signed and Sealed this

Thirtieth Day of May, 1995

Attest:

BRUCE LEHMAN

Attesting Officer      Commissioner of Patents and Trademarks